US005708593A

United States Patent [19]

Saby et al.

[11] Patent Number: 5,708,593
[45] Date of Patent: Jan. 13, 1998

[54] METHOD FOR CORRECTING A SIGNAL DELIVERED BY A MEASURING INSTRUMENT

[75] Inventors: Claude-Alain Saby, Bron; Philippe Ricoux, Brignais, both of France

[73] Assignee: Elf Antar France, Courbevoie, France

[21] Appl. No.: 650,715

[22] Filed: May 20, 1996

[30] Foreign Application Priority Data

May 19, 1995 [FR] France .................... 95 05957

[51] Int. Cl.[6] ........................... G06F 15/20
[52] U.S. Cl. .................... 364/571.04; 364/571.02; 364/571.01; 364/498; 324/601
[58] Field of Search .............. 364/571.04, 571.02, 364/481, 498, 550, 571.01; 324/601, 307, 76.11, 130; 73/1 R

[56] References Cited

U.S. PATENT DOCUMENTS

| | | | |
|---|---|---|---|
| Re. 34,070 | 9/1992 | Regimand | 364/571.02 |
| 4,752,868 | 6/1988 | Nicholas et al. | 364/550 |
| 4,864,842 | 9/1989 | Regimand | 364/571.04 |
| 4,866,644 | 9/1989 | Shenk et al. | 364/553 |
| 5,121,337 | 6/1992 | Brown | 364/571.04 |
| 5,243,546 | 9/1993 | Maggard | 364/571.02 |
| 5,446,681 | 8/1995 | Gethner et al. | 364/571.04 |
| 5,559,728 | 9/1996 | Kowalski et al. | 364/571.02 |
| 5,568,400 | 10/1996 | Stark et al. | 364/571.02 |
| 5,572,125 | 11/1996 | Dunkel | 324/307 |

*Primary Examiner*—Emanuel T. Voeltz
*Assistant Examiner*—Bryan Bui
*Attorney, Agent, or Firm*—Oblon, Spivak, McClelland, Maier & Neustadt, P.C.

[57] ABSTRACT

A method for correcting a signal delivered by a slave measuring instrument with respect to a reference signal delivered by a master measuring instrument of the same type involved in the analyzing of the same product includes the provision of standardization signals delivered by both the slave instrument and the master instrument as they analyze calibration products, each calibration product having a particular known calibration characteristic. These standardization signals are subjected to series decomposition so that they are simplified prior to their being formed into a correction coefficient matrix useful in correcting a signal derived from a slave measuring instrument performing an actual analysis of the characteristic of a test product like the calibration products. When a test product undergoes analysis, it is analyzed by the slave measuring instrument to determine a signal which is then subject to a further series decomposition and correction with the aid of the stored correction matrix. Once corrected, the signal is subject to recomposing and a final determination of the characteristic of concern using a calibration model established relative to the master measuring instrument and the known characteristics of calibration products.

20 Claims, No Drawings

METHOD FOR CORRECTING A SIGNAL DELIVERED BY A MEASURING INSTRUMENT

BACKGROUND OF THE INVENTION

1. Field of the Invention

The invention relates to a method for correcting a signal delivered by a slave measuring instrument with respect to a signal delivered by a master measuring instrument of the same type, in order to use for the slave instrument a calibration model established beforehand for the master instrument.

It finds its application in monitoring laboratories, research laboratories, production units and manufacturing units for the chemical, petroleum, petrochemical, pharmaceutical, cosmetics and agro-foodstuffs industries.

2. Discussion of Background

Many instruments for measuring physical or chemical characteristics, for example spectrometers, require calibration.

This calibration consists in establishing a model which represents the mathematical relationship between a characteristic of a product analysed and the signal delivered by the instrument as the result of an analysis of this product.

This calibration operation is time-consuming and requires the use of several tens of products, and preferably more than 100, the characteristics of which are determined by direct measurements.

Once this calibration operation has been carried out for a given instrument, it is particularly beneficial to use the model obtained for another instrument of the same type, in order to avoid repeating the calibration operations once more. Experience shows that if this procedure is adopted, without making corrections, the results obtained are not satisfactory.

This is because such a procedure does not make it possible to take into account the differences in instrument responses between the two instruments, which always exist in practice.

In the case of instruments such as infrared spectrometers, these differences may be attributed to different light sources, different optical systems, different detectors and, in general, the different characteristics of the components of the instruments.

The instrument response of a given instrument also varies over time, for example as a function of temperature, ageing of the components and the degree to which they accumulate contaminants. These instruments generally have a tendency to drift.

In order to overcome these drawbacks, one method for transferring the spectra from a master optical instrument to a slave optical instrument is described in U.S. Pat. No. 4,866,644.

This method includes the following steps:

—Step 1: selection of a set of standardization products representing the products to be analysed, —Step 2: derivation of spectras obtained from the set of standardization products, —Step 3: choice, for each wavelength of the master instrument, of a spectral window in the neighbouring wavelengths of the slave instrument, —Step 4: establishment of a quadratic model associating the wavelengths of the master instrument with the wavelengths of the slave instrument, —Step 5: calculation by interpolation of the responses to the spectra delivered by the slave instrument at the wavelengths suggested by the quadratic model, —Step 6: calculation of the correction in the spectral intensity to be made to the signals from the slave instrument by linear regression for each wavelength, on the signals from the master instrument at the corresponding wavelengths, —Step 7: establishment of a standardization file in which correction factors, wavelength indices and spectral intensities are stored.

Each spectrum obtained using the slave instrument supplied with the product to be analysed is standardized by using the standardization file.

The method set out above is complex and difficult to use for the following reasons:

—subjective definition of the spectral windows for the slave instrument,

—correlation of each wavelength of the master instrument with the wavelengths of the spectral window of the slave, —establishment of a quadratic model for associating the wavelengths of the master instrument with the wavelengths of the slave.

This method furthermore has the following drawbacks:

—it makes it necessary to work with a number of standardization product signals which is preferably greater than 10, —it does not take into account the drift in the signal delivered by the slave instrument, or local artefacts, and consequently does not make it possible to correct them, —it requires preliminary transformations of the signals by derivation and leads to the manipulation of number matrices of large dimension, for example 100 lines, 1000 columns, —finally, if the differences between the spectra output by the master and slave instruments are very small, the results are highly erroneous.

DESCRIPTION OF THE INVENTION

The object of the present invention is, precisely, to overcome these drawbacks and, in particular, to provide a method for correcting a signal delivered by a slave measuring instrument with respect to a signal delivered by a master instrument, which method is easy to use and simple to comprehend.

This method can be used both in monitoring and research laboratories and for determining the characteristics of a product during manufacture. To this end, the invention provides a method for correcting a signal delivered as a result of an analysis by a slave measuring instrument with respect to a signal delivered by a master measuring instrument of the same type, the said instruments making it possible to determine a characteristic of a product analysed, by means of a calibration model of the master instrument, establishing the relationship between the signal obtained with the said product and the desired characteristic, the said method consisting in establishing the calibration model on the basis of a plurality of calibration products with known characteristics and in processing each of the standardization signals obtained from a plurality of products of the same type as the calibration products, characterized in that it includes, on the one hand, the following preliminary steps:

—series decomposition of each of the standardization signals delivered by the master and slave instruments, —establishment of mathematical relationships between the parameters resulting from the series decompositions of the said signals, —determination of the correction coefficients for the parameters resulting from the series decomposition of the signals from the slave instrument with respect to the parameters resulting from the series decomposition of the signals from the master instrument, by using the said mathematical relationships, —storing the said correction coefficients in the form of a correction matrix, and, on the other hand, the following steps:

—series decomposition of a signal delivered by the slave instrument supplied with the product analysed, —correction of the coefficients resulting from the series decomposition, with the aid of the correction matrix, —recomposition of the signal delivered by the slave instrument supplied with the product analysed, after correction of the coefficients in the form of a corrected signal, —determination of the desired characteristic of the product analysed by the slave instrument with the aid of the calibration model applied to the corrected signal.

DETAILED DESCRIPTION OF THE INVENTION

In general, the method according to the invention makes it possible to correct the signals delivered by instruments used for determining characteristics of the products to be analysed.

By way of nonlimiting example, mention may be made of infrared, near infrared and mid-range infrared spectrometers, mass spectrometers, nuclear magnetic resonance spectrometers and ultraviolet spectrometers.

The method of the invention consists, prior to the use of a slave instrument for determining a characteristic of a product analysed:

—in establishing a calibration model on the basis of the signals output by a master measuring instrument of the same type as the slave, by using a set of calibration products whose characteristics are precisely known, —then in processing the standardization signals delivered by the master measuring instrument and the slave measuring instrument, each of them being supplied with the same set of standardization products representing the characteristics which have been subjected to calibration.

The method of the invention then consists in decomposing into series each of the standardization signals delivered respectively by the master and slave measuring instruments.

In this way it is possible to eliminate the high components, which contain no useful information, from the decompositions of the signals, which makes it possible to reduce the number of coefficients used to represent the signals.

The decomposition method is chosen from those methods which make it possible to recalculate the original signals from the elements obtained by the decomposition, using a function of the inverse type.

The following step in the method of the invention consists in establishing mathematical relationships between the coefficients obtained by the series decomposition of the signals delivered respectively by the master instrument and the slave instrument.

Correction coefficients for the parameters resulting from the decomposition of the signals from the slave instrument with respect to the parameters resulting from the decomposition of the signals from the master instrument are then determined by using the mathematical relationships established in the previous step.

The correction coefficients thus determined are stored in the form of a correction matrix.

Once these steps of calibration, standardization and determining the matrix of the correction coefficients have been carried out, this correction matrix is used to correct a signal delivered as the result of an analysis by the slave measuring instrument, by carrying out the following steps:

—series decomposition of a signal delivered by a slave instrument supplied with the product analysed, —correction of the coefficients resulting from the series decomposition, with the aid of the correction matrix, —recomposition of the signal delivered by the slave instrument supplied with the product analysed, after correction of the coefficients in the form of a corrected signal, —determination of the desired characteristic of the product analysed by the slave instrument with the aid of the calibration model applied to the corrected signal.

This method only uses objective elements and simple methods, it makes it possible to work with a small number of standardization signals, for example fewer than ten, and it makes it possible to overcome any drift in the signal, the presence of local artefacts and the presence of noise, by virtue of the signal processing possibilities.

This method manipulates matrices of small dimension, for example thirty columns after decomposition of the signal, in comparison with the thousand columns manipulated by methods which do not decompose the signal, and 10 lines corresponding to the number of standardization signals, in comparison with the 100 required for known methods.

In order to verify the validity of the coefficients of the correction matrix, the value of the characteristic of at least one validation product, obtained from the signal delivered by the slave instrument then corrected according to the method of the invention, is compared with the value of this same characteristic, obtained for the same validation product from the signal delivered by the master instrument.

This verification takes place as follows:

—the signal delivered by the slave instrument, obtained from a validation product, is decomposed into series, —the parameters of the preceding decomposition are corrected by using the correction matrix, —the signal delivered by the slave instrument is recomposed in order to obtain the corrected signal, —the characteristic of the validation product is determined with the aid of the calibration model applied to the corrected signal, —finally, the fact that the value obtained is substantially equal to the value of the characteristic obtained for the same validation product from the signal delivered by the master instrument with the same calibration model is verified.

According to another characteristic of the invention, the method is used to correct the signal delivered by the master instrument at a given time, with respect to the signal delivered by the same instrument at a prior period of time. The same instrument, used at different periods of time, is thus successively the slave instrument and the master instrument. In this way, the method makes it possible to correct the drifts of an instrument over time. These drifts may, for example, result from accumulation of contaminants, from ageing, from temperature variations and, more generally, from the operating conditions of the instrument which change over time.

According to a particular embodiment of the invention, the series decomposition of the standardization signals delivered by the master and slave instruments is carried out using the Fourier transform.

Thus, by virtue of this transform, the signals delivered by the instruments, expressed in the time domain, are represented in the frequency domain.

The series decomposition is expressed as follows:

$$X(f) = \int_{-\infty}^{+\infty} x(t)\cos 2\pi ft\, dt - i \int_{-\infty}^{+\infty} x(t)\sin 2\pi ft\, dt$$

x(t) is the signal delivered by an instrument, expressed as a function of time, t represents time, f represents the frequencies, X(f) is the signal delivered by the measuring instrument, represented in the frequency domain.

In discrete form, the Fourier transform is expressed as follows:

$$F(k) = 1/n \sum_{i=0}^{n-1} y_i \exp(-j2\pi ik/n)$$

in which the $y_i$ are the measured values of a signal decomposed into n points

F(k) are the values resulting from the Fourier transform k and i vary from 0 to n−1 n represents the number of points in the signal, determined experimentally.

By fixing the value of n at a few tens, for example 30, the coefficients of higher ranks are eliminated, which has an effect of filtering and eliminating noise.

By applying this transform, two series of coefficients are obtained for each signal, the real coefficients r, $r_1$, $r_2$, $r_3$, . . . $r_n$ and imaginary coefficients $k_1$, $k_2$, $k_3$, . . . $k_n$.

Applying the inverse Fourier transform makes it possible to recompose the slave instrument signals, corrected with respect to the master instrument, by recomposition, from the real and imaginary coefficients of the signals from the slave instrument corrected by the established mathematical relationships.

The discrete inverse Fourier transform is expressed by the following equation:

$$z_i = 1/n \sum_{k=0}^{n-1} F(k)\exp(+j2\pi ik/n)$$

in which the $z_i$ are the recomposed values of the signal n represents the number of points in the signal, determined experimentally.

k and i vary from 0 to n−1

F(k) are the values resulting from the Fourier transform.

According to another particular embodiment of the invention, the series decomposition of the signals is carried out by a wavelet decomposition algorithm. In this case, the signal delivered by the measuring instrument is sampled and decomposed into a sum of localized functions which are associated with different timescales. First, the decomposition base may or may not be an orthonormal base. The integral of each wavelet is equal to zero, according to the following expression:

$$\int_{-\infty}^{+\infty} \psi_r(x)\, dx = 0$$

in which $\psi_r(x)$ denotes a wavelet function.

The benefit of the wavelet decomposition over the Fourier series decomposition resides in the fact that each coefficient characterizes the original signal, and thus makes it possible to work with a small number of coefficients. The recomposition for obtaining the corrected signals is carried out by a wavelet reconstruction algorithm.

According to another characteristic of the invention, the mathematical relationships between the parameters resulting from the series decompositions are linear relationships represented by the following equation:

$$B = \alpha + \beta \times A$$

in which:

B represents the matrix of the coefficients obtained by the series decomposition of the signals delivered by the slave instrument, A represents the matrix of the coefficients obtained by the series decomposition of the signals delivered by the master instrument, $\alpha$ and $\beta$ are respectively the matrices of slope coefficients and intercept coefficients which are estimated by a regression algorithm.

According to another characteristic of the invention, the mathematical relationships between the parameters resulting from the series decompositions are polynomial relationships, of order at least equal to 2, represented by the following equation:

$$B = g + \sum_{i=0}^{p} h(i) \times A^i$$

in which:

B represents the matrix of the coefficients obtained by the series decomposition of the signals delivered by the slave instrument, A represents the matrix of the coefficients obtained by the series decomposition of the signals delivered by the master instrument, g and h(i) are matrices of coefficients estimated by a regression algorithm p is greater than or equal to 2 and less than n.

According to another characteristic of the invention, the mathematical relationships between the parameters resulting from the series decompositions are chosen from algorithms representing growth curves, such as, for example, the following functions:

—exponential: $y = \alpha \beta^t$

—modified exponential: $y = \alpha \beta^t + \eta$

—Gompertz $y = \exp(\alpha \beta^t + \eta)$

—logistic $y = 1/(\alpha \beta^t + \eta)$ in which the coefficients $\alpha$, $\beta$ and $\eta$ are estimated by a regression algorithm.

According to another characteristic of the invention, the regression algorithm used for determining the matrices of coefficients which are involved in the mathematical relationships between the parameters resulting from the series decompositions are linear or nonlinear algorithms using a convergence criterion, such as the least squares or maximum likelihood criteria, for example.

According to another characteristic of the invention, the mathematical relationships between the parameters resulting from the series decomposition are represented by neural networks. Neural networks are beneficial because, on the one hand, they provide learning capacities which make it possible to adapt the relationships between the calibration signals and, on the other hand, they take into account the nonlinearities between the responses of the master and slave instruments. This characteristic will be better understood on referring to the example described below.

An example of mathematical relationships established by neural networks:

—a neural network with 3 layers is used,

—the input and output layers contain 35 neurons (number of coefficients in the Fourier transform of the signals from the slave instrument, at input, and from the master instrument, at output), —a hidden layer makes it possible to learn the correspondence function, —the neuron activation functions are sigmoids and the learning algorithm uses the gradient retro-propagation method, —two different networks make it possible to learn the correspondence for the real and imaginary coefficients, —for the case mentioned, an architecture composed of five neurons is adopted for the hidden layer.

We claim:

1. Method for correcting a signal delivered as a result of an analysis of a characteristic of a test product by a slave measuring instrument, said method comprising:

establishing a calibration model for a master measuring instrument of a same type as the slave measuring instrument on the basis of a plurality of calibration products each being of a same type as the test product and having a known calibration characteristic;

using said slave measuring instrument and said master measuring instrument of the same type to deliver slave standardization signals and master standardization signals as to each of the calibration products;

performing a series decomposition of each of the master instrument and slave instrument standardization signals delivered respectively by the master and slave instruments for each of the calibration products;

establishing mathematical relationships between parameters resulting from the series decompositions of the master and slave standardization signals;

using the established mathematical relationship to determine correction coefficients for the parameters resulting from the series decomposition of the slave standardization signals delivered from the slave instrument with respect to similar parameters resulting from the series decomposition of the master standardization signals delivered from the master instrument for each calibration product;

storing the correction coefficients in the form of a correction matrix;

using the slave instrument to analyze a test product;

performing a series decomposition of a resulting test product signal delivered by the slave instrument;

correcting coefficients resulting from the series decomposition of the signal delivered by the slave instrument using the stored correction matrix;

using the corrected coefficients in recomposing a corrected version of the signal delivered by the slave instrument analyzing the characteristic of the test product; and determining the desired characteristic of the test product analyzed by the slave instrument by applying the calibration model to the corrected version of the signal delivered by the slave instrument.

2. Method according to claim 1, comprising:

verifying the validity of the correction coefficients by executing the following steps, performing a validation series decomposition of at least one validation signal delivered by the slave instrument, said at least one validation signal being obtained from the analysis of at least one validation product, correcting the parameters of the validation series decomposition by using the correction matrix;

recomposing the validation signal delivered by the slave instrument in order to obtain the corrected signal, determining the value of a characteristic of the validation product using the calibration model applied to the corrected signal, verifying that the characteristic of the validation product value is substantially equal to the value of the characteristic determined for the same validation product from the signals delivered by the master instrument using the same calibration model.

3. Method according to claim 2, wherein the slave instrument and the master instrument are the same instrument, used at different periods of time.

4. Method according to claim 2, wherein the series decompositions are carried out by using Fourier transforms and the recomposing steps are carried out by using inverse Fourier transforms.

5. Method according to claim 2, wherein the series decomposition and the recomposing steps are carried out by wavelet decomposition and reconstruction algorithms.

6. Method according to claim 2, wherein the mathematical relationships between parameters resulting from the series decompositions are linear relationships whose coefficients are estimated by a regression algorithm.

7. Method according to claim 2, wherein the mathematical relationships between the parameters resulting from the series decompositions are polynomial relationships, of order at least equal to 2, whose coefficients are estimated by a regression algorithm.

8. Method according to claim 1, wherein the slave instrument and the master instrument are the same instrument, used at different periods of time.

9. Method according to claim 8, wherein the series decompositions are carried out by using Fourier transforms and the recomposing step is carried out by using an inverse Fourier transform.

10. Method according to claim 8, wherein the series decomposition and the recomposition steps are carried out by wavelet decomposition and reconstruction algorithms.

11. Method according to claim 8, wherein the mathematical relationships between parameters resulting from the series decompositions are linear relationships whose coefficients are estimated by a regression algorithm.

12. Method according to claim 8, wherein the mathematical relationships between the parameters resulting from the series decompositions are polynomial relationships, of order at least equal to 2, whose coefficients are estimated by a regression algorithm.

13. Method according to claim 1, wherein series decompositions are carried out by using Fourier transforms and the recomposing step is carried out by using an inverse Fourier transform.

14. Method according to claim 13, wherein the mathematical relationships between parameters resulting from the series decompositions are linear relationships whose coefficients are estimated by a regression algorithm.

15. Method according to claim 1, wherein series decompositions and the recomposing steps are carried out by wavelet decomposition and reconstruction algorithms, respectively.

16. Method according to claim 1, wherein the mathematical relationships between the parameters resulting from the series decompositions are linear relationships whose coefficients are estimated by a regression algorithm.

17. Method according to claim 16, wherein the regression algorithm is a linear or nonlinear algorithm.

18. Method according to claim 1, wherein the mathematical relationships between the parameters resulting from the series decompositions are polynomial relationships, of order at least equal to 2, whose coefficients are estimated by a regression algorithm.

19. Method according to claim 1, wherein the mathematical relationships between the parameters resulting from the series decompositions are relationships chosen from the relationships representing growth curves whose coefficients are estimated by a regression algorithm.

20. Method according to claim 1, wherein the mathematical relationships between the parameters resulting from the series decompositions are represented by neural networks.

* * * * *